US008593635B2

(12) United States Patent  
Ray et al.

(10) Patent No.: US 8,593,635 B2
(45) Date of Patent: Nov. 26, 2013

(54) CAMERA WEB SUPPORT

(75) Inventors: Paul C. Ray, San Diego, CA (US);
Madhu Babu, Escondido, CA (US);
Nadeem E. Khan, San Diego, CA (US);
Raul A. Sumera, Chula Vista, CA (US);
Robert W. Braun, Appleton, WI (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 291 days.

(21) Appl. No.: 13/119,705

(22) PCT Filed: Oct. 1, 2008

(86) PCT No.: PCT/US2008/078514
§ 371 (c)(1),
(2), (4) Date: Mar. 17, 2011

(87) PCT Pub. No.: WO2010/039135
PCT Pub. Date: Apr. 8, 2010

(65) Prior Publication Data
US 2011/0170101 A1    Jul. 14, 2011

(51) Int. Cl.
*G01N 21/89* (2006.01)
(52) U.S. Cl.
USPC .................. 356/429; 356/430; 250/548
(58) Field of Classification Search
USPC ............ 356/429–431, 237.1–237.5; 400/611;
101/228, 424.1, 488; 250/548
See application file for complete search history.

(56) References Cited

U.S. PATENT DOCUMENTS

| 4,385,716 A * | 5/1983 | De Roeck et al. ............... 226/18 |
| 5,095,214 A * | 3/1992 | Eder ......................... 250/559.03 |
| 5,455,764 A | 10/1995 | Meihofer |
| 6,266,437 B1 | 7/2001 | Eichel et al. |
| 6,436,465 B1 * | 8/2002 | Tsunoda et al. ................... 427/8 |
| RE38,957 E * | 1/2006 | Laussermair et al. .......... 399/16 |
| 8,348,531 B2 * | 1/2013 | Godden et al. ................ 400/611 |
| 8,353,147 B2 * | 1/2013 | Sprehe et al. .................... 53/551 |
| 2001/0027730 A1 | 10/2001 | Kamoda |
| 2001/0054364 A1 | 12/2001 | Kusaka |
| 2004/0045996 A1 * | 3/2004 | Lamothe .................... 226/118.3 |
| 2004/0051061 A1 | 3/2004 | Warner |
| 2004/0145727 A1 | 7/2004 | Tsukamto et al. |
| 2007/0175912 A1 | 8/2007 | Uehara et al. |
| 2008/0035777 A1 * | 2/2008 | Benvenuti ..................... 242/364 |
| 2011/0239879 A1 * | 10/2011 | Denninger et al. ........... 101/217 |
| 2013/0068874 A1 * | 3/2013 | Schwamberger et al. . 242/526.1 |

FOREIGN PATENT DOCUMENTS

| EP | 1834779 | 9/2007 |
| JP | 06082388 | 3/1994 |
| JP | 10190952 | 7/1998 |
| JP | 2000209400 | 7/2000 |
| JP | 2002139446 | 5/2002 |
| JP | 2003344302 | 12/2003 |
| JP | 2006015755 | 1/2006 |

* cited by examiner

*Primary Examiner* — Hoa Pham

(57) ABSTRACT

Web supports (30, 32, 34, 36, 38, 330, 332, 334, 336, 338, 340) form a first web path (46, 48, 346, 348) in which a web is presented opposite to a camera (26, 326) and an alternative second web path (46, 48, 346, 348) in which the web (230) is overturned prior to being presented opposite to the camera (26, 326).

20 Claims, 6 Drawing Sheets

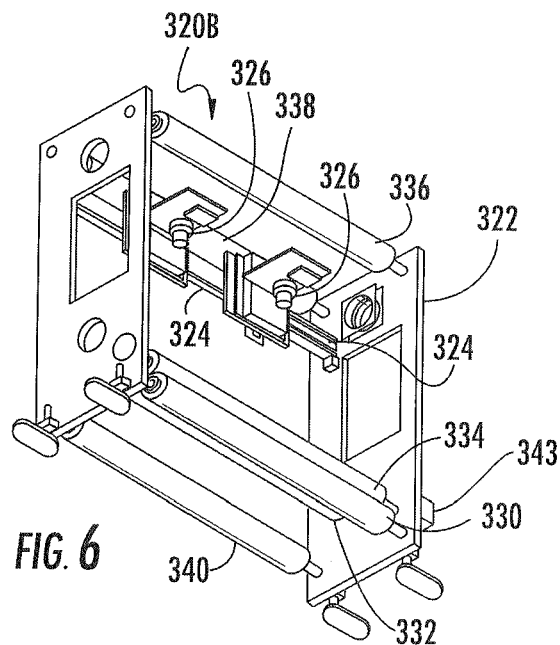
FIG. 6
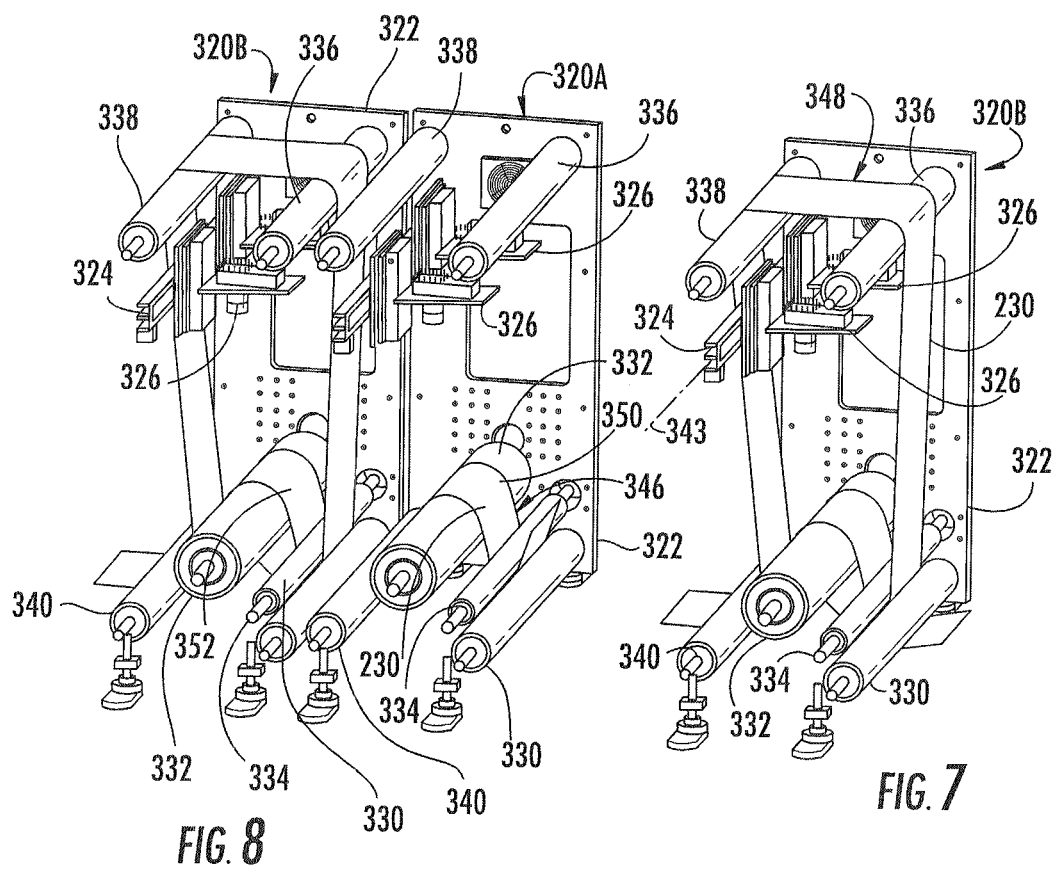
FIG. 7
FIG. 8

CAMERA WEB SUPPORT

BACKGROUND

Vision systems are sometimes used to verify print quality. Existing vision systems may require excessive force base, excessive complexity and customization.

BRIEF DESCRIPTION OF THE DRAWINGS

FIG. 6 is a bottom perspective view of a vision system module of the duplexing system of FIG. 3 according to an example embodiment.

FIG. 7 is a top perspective view of the vision system module of FIG. 6 further illustrating a web being directed along a first web path according to an example embodiment.

FIG. 8 is a top perspective view of two substantial identical vision system modules further illustrating a web being directed along a first web path and a second web path according to an example embodiment.

DETAILED DESCRIPTION OF THE EXAMPLE EMBODIMENTS

Figure 1:
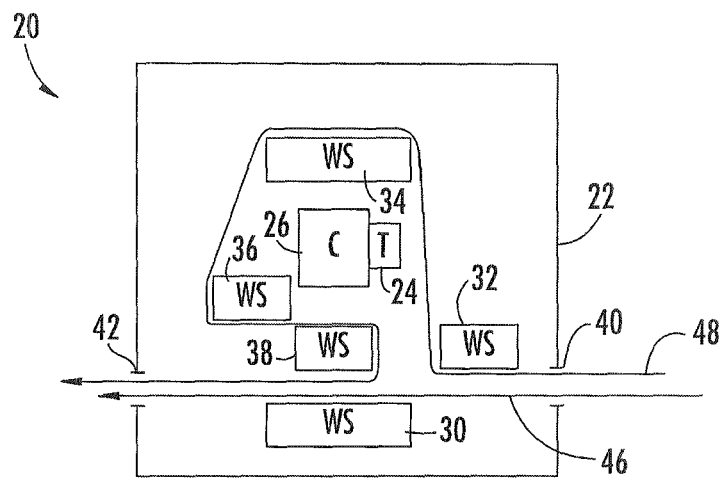
FIG. 1 is a schematic illustration of a vision system module according to an example embodiment.

FIG. 1 schematically illustrates a vision system module 20 according to an example embodiment. As will be described hereafter, vision system module 20 is compact, is relatively less complex and is versatile. Vision system module 20 may be combined with another substantially identical module 20 to facilitate print quality verification on both sides of a web without the web having to be overturned prior to receipt by either of modules 20.

Vision system module 20 includes frame or enclosure 22, track 24, camera 26, and web supports 30, 32, 34, 36 and 38. Enclosure 22 comprises one or more structures configured to support or at least partially enclose the remaining elements or components of vision system module 20. In the example illustrated, enclosure 22 substantially surrounds and completely encloses remaining components of vision system module 20. Enclosure 22 includes inlet 40 and outlet 42. Inlet 40 and outlet 42 comprise openings in walls of enclosure 22 for which a web enters and leaves enclosure 22 and vision module 20, respectively. Because enclosure 22 supports each of the remaining components of vision system module 20, vision system module 20, when not receiving a web, may be transported, stored and repositioned as a self-contained unit independent of any other components or modules of a printing system. This modularity provides module 20 with enhanced versatility and increased flexibility with respect to a layout or arrangement of a printing system.

Track 24 comprises one or more structures configured to movably support camera 26 with respect to a web passing through module 20. In one embodiment, track 24 is configured to movably support camera 26 along an axis across a web, transverse to a direction in which the web is moving. In another embodiment, track 24 may be configured to movably support camera 26 along an axis potentially parallel to the direction in which the web is moving. In one embodiment, track 24 may comprise a bar having opposite grooves which slidably receive corresponding opposing projections or tongues extending from camera 26. In another embodiment, the sliding movement of camera 26 along track 24 may be facilitated by low friction surfaces or bearings. Because track 26 movably supports camera 26 with respect to a web passing through module 20, camera 26 may be repositioned with respect to the web to sense images or printing upon various portions of a face of a web or to accommodate different web widths. In yet another embodiment, track 24 may be omitted, wherein camera 26 is stationarily supported by enclosure 22 or rotates with respect to enclosure 22.

Camera 26 comprises one or more image capture devices configured to sense or capture printing or other images upon a surface, such as a face of a web passing through module 20. Electrical signals representing a captured image are then transmitted from camera 26 to a processor, computer or other device for analysis and potentially used in improving print quality. In one embodiment, camera 26 may comprise one or more video or still image charge coupled sensing devices. In other embodiments, other sensing cameras may be employed.

Web supports 30-38 comprise structures configured to support and direct a web through vision system module 20 and relative to camera 26 while allowing a face of the web to be sensed by camera 26. Web supports 30-38 may comprise rollers, platens, belts, stationary straight or curved web contacting panels, web contacting bearing surfaces or structures and the like. In particular embodiments, some of web supports 30-38 may be additionally configured to grip and drive a web along an associated web path. Web supports 30-38 form, define or provide a first web path 46 in which a web is presented opposite camera 26 and a second alternative web path 48 in which the web is overturned prior to being presented opposite to camera 26. Because web supports 30-38 provide two alternative web paths 46, 48, regardless of the orientation of the web as it enters module 20, module 20 may be used to sense either face of a web depending upon which path the web takes through module 20. Consequently, module 20 is extremely versatile, allowing either face of a web to be sensed or allowing two substantially identical modules to be combined for sensing both faces of a web.

In the particular example illustrated, the one or more web supports 30 form web path 46 while web supports 32-38 form web path 48. In particular, following web path 46, a web enters enclosure 22 through inlet 40, travels across the one or more web supports 30 opposite to camera 26 and exits enclosure 22 through outlet 42. During such time, camera 26 is opposite to the web so as to sense a face of the web. The one or more web supports 38 are offset so as to not interfere with or impair the vision or view of the web along web path 46 by camera 26. Although web path 46 is illustrated as extending linearly from inlet 40 to outlet 42, in other embodiments, web path 46 may alternatively be serpentine. In some embodiments, web path 46 may be configured such that the web at least partially wraps about one or more rollers, plates, bearings or other structures providing the one or more web supports 30 prior to being discharged through outlet 42 so long as the web is not overturned from inlet 40 prior to being presented opposite to camera 26 and prior to being sensed by camera 26.

Web path 48 enters enclosure 22 through inlet 40 and is defined by web supports 32-38 so as to extend over and around camera 26 prior to being presented opposite to camera 26 for image capture by camera 26. The one or more web supports 32 direct the web across a side of camera 26 between a top of enclosure 22 and camera 26 to web supports 34. Web supports 34 direct the web over a top of camera 26 on an opposite side of camera 26 as its aperture, lens or sensing face. From the one or more web supports 34, the web is supported to web supports 36. The one or more web supports 36 overturn the web and present the web opposite to the aperture, lens or sensing face of the camera 26. Overall, web supports 34 and 36 cooperate to flip the web such that an opposite face of the web is presented for sensing by camera 26. After such sensing, the one or more web supports 38 overturn the web once again such that the web leaves enclosure 22 through outlet 42 in the same orientation as the orientation in which the web entered enclosure 22. Web supports 38 further enable the web to pass through module 20 in a serial fashion, wherein web enters enclosure 22 on a first side of enclosure 22 and exits enclosure 22 of module 20 on a second opposite side of enclosure 22. As a result, module 20 may be arranged in an end-to-end/or serial fashion with respect to other modules or components of the printing or duplexing system.

Although module 20 is illustrated as having four general groupings of one or more web supports, in other embodiments, module 20 may have a greater or fewer of such groupings of web supports. Although module 20 is illustrated as having distinct web supports forming paths 46 and 48, in other embodiments, paths 46 and 48 may share one or more web supports. Although module 20 is described as being arranged in the noted fashion to provide the noted benefits, in other embodiments, module 20 may have alternative configurations or architectures. For example, in other embodiments, module 20 may be configured such that the web enters and exits through a same side of enclosure 22 or such that the web enters enclosure 22 with a first orientation and is discharged from enclosure 22 with a second opposite orientation (i.e., entering face up and exiting face down or vice versa).

Figure 2:
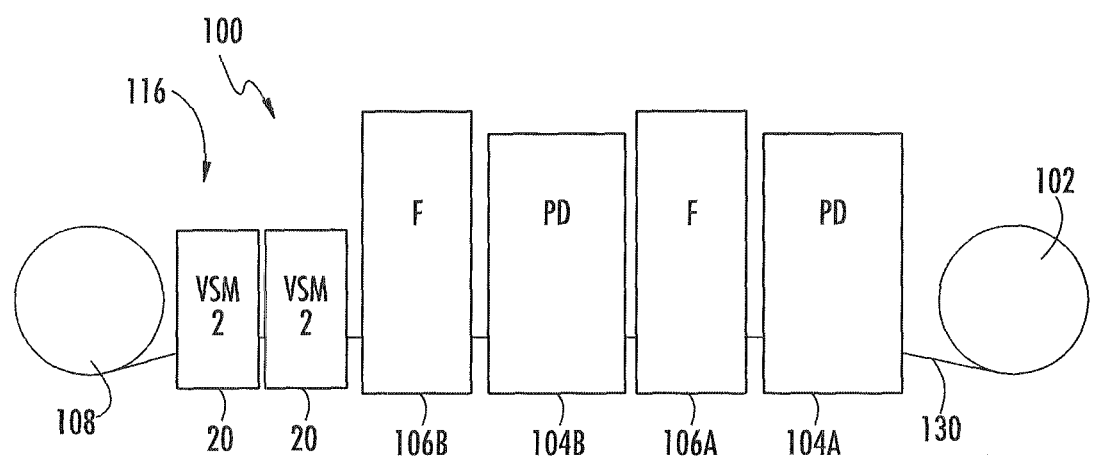
FIG. 2 is a schematic illustration of a duplexing system including a pair of the vision system modules of FIG. 1 according to an example embodiment.

FIG. 2 illustrates one example of the versatility provided by vision system module 20 of FIG. 1. FIG. 2 schematically illustrates duplexing system 100 including vision system 116 formed from two vision system modules 20. Duplexing system 100 performs duplex printing (printing on both sides or faces of a web). Using vision system 116, duplexing system 100 is further able to verify the print performance or print quality achieved on both faces of web 130. As a result, enhanced quality control is achieved and adjustments may potentially be made to duplexing system 100 to enhance its printing performance.

In addition to vision system 116, duplexing system 100 includes web supply 102, print devices 104A and 104B (collectively referred to as print devices 104), image fixers 106A and 106B (collectively referred to as image fixers 106) and web collection 108. Web supply 102 comprises a device configured to supply web 130. An example of a web supply 102 comprises a supply reel, roll or spool of material configured to be printed upon.

Print devices 104 comprise devices configured to print or otherwise form images upon web 130. In one embodiment, print devices 104 are configured to deposit fluid ink onto web 130. For example, in one embodiment, print devices 104 may comprise drop-on-demand inkjet printers. In one embodiment, print devices 104 are configured to deposit multiple colors of ink onto web 130. In yet another embodiment, print devices 104 may be configured to form images or patterns upon web 130 in other manners. For example, in other embodiments, print devices 104 may comprise dry toner electrophotographic printing devices or liquid toner electrophotographic printing devices. In still other embodiments competent devices 104 may comprise other printing mechanisms.

In the example illustrated, print device 104A is configured to deposit multiple colors of fluid ink onto a first face of web 130. Print device 104 is configured to deposit multiple colors of fluid ink onto a second opposite face of web 130. Prior to printing by print device 104B, web 130 is overturned to facilitate printing on the second opposite face. In one embodiment, such overturning may be performed by print device 104A, by print device 104B, by image fixer 106A or by an additional web overturning module or device between print device 104A and 104B (not shown).

Image fixers 106 comprise devices configured to facilitate drying, solidification or curing of the materials printed or deposited upon web 130. In one embodiment, fixers 106 may comprise devices configured to heat the printed upon web 130. In another embodiment, image fixers 106 may be configured to direct air across or onto web 130. In such an embodiment, the air may be heated. In another embodiment, fixers 106 may be configured to apply electromagnetic radiation, such as microwaves, to facilitate drying, curing or solidification of the printing material upon web 130. In the example illustrated, image fixer 106A is configured to dry the material printed or deposited upon the first face of web 130 by print device 104A. Likewise, image fixer 106B is configured to dry the material printed or deposited upon the second opposite face of web 130 by print device 104B. In yet other embodiments, one or both of image fixers 106A, 106B may be omitted where the printing material is sufficiently dry, solidified or cured without such fixers.

Web collection 108 comprises a device configured to reel in or gather printed upon web 130 after web 130 has been inspected by vision system 116. In the example illustrated, web collection 108 comprises a take-up reel, reel or spool. In one embodiment, web collection 108 is driven so as to assist in pulling web 130 through vision system 116. In other embodiments, web collection 108 may be replaced with other mechanisms for handling a printed upon web 130. For example, instead of being wound about a spool or reel, the printed upon web 130 may be folded, cut, stapled, bound or otherwise handled.

Vision system 116 senses printing upon both sides of web 130 to verify the printing accuracy or quality (color and/or location of the printing). As noted above, vision system includes two substantially identical vision system modules 20 positioned end-to-end downstream of the last printing device 104B and the last image fixer 106B. One of the vision system modules 20 of vision system 116 directs web 130 along web path 46 while the other of vision system modules 20 of vision system 116 directs web 130 along web path 48. As a result, both sides or faces of web 130 are inspected.

Because vision system modules 20 are substantially identical, modules 20 are more easily inserted into duplexing system 100 with less customization. Because modules 20 are substantial duplicates of one another, vision system 116 is less complex and has fewer parts, simplifying repair and replacement. For example, should one module 20 fail or need repair or replacement, another module 20 may be easily inserted in its place. As a result replacement or substitute modules 20 may be easily inventoried and used when needed to reduce downtime of duplexing system 100. In addition, modules 20 may alternatively be provided at other locations along the duplexing system 100. For example, the particular module 20 which inspects the first side of web 130 may alternatively be located between print devices 104A and 104B. Such a reconfiguring of the line of components forming duplexing system 100 may be achieved without substantial alteration or modification of either of modules 20 of vision system 116.

Figure 3:
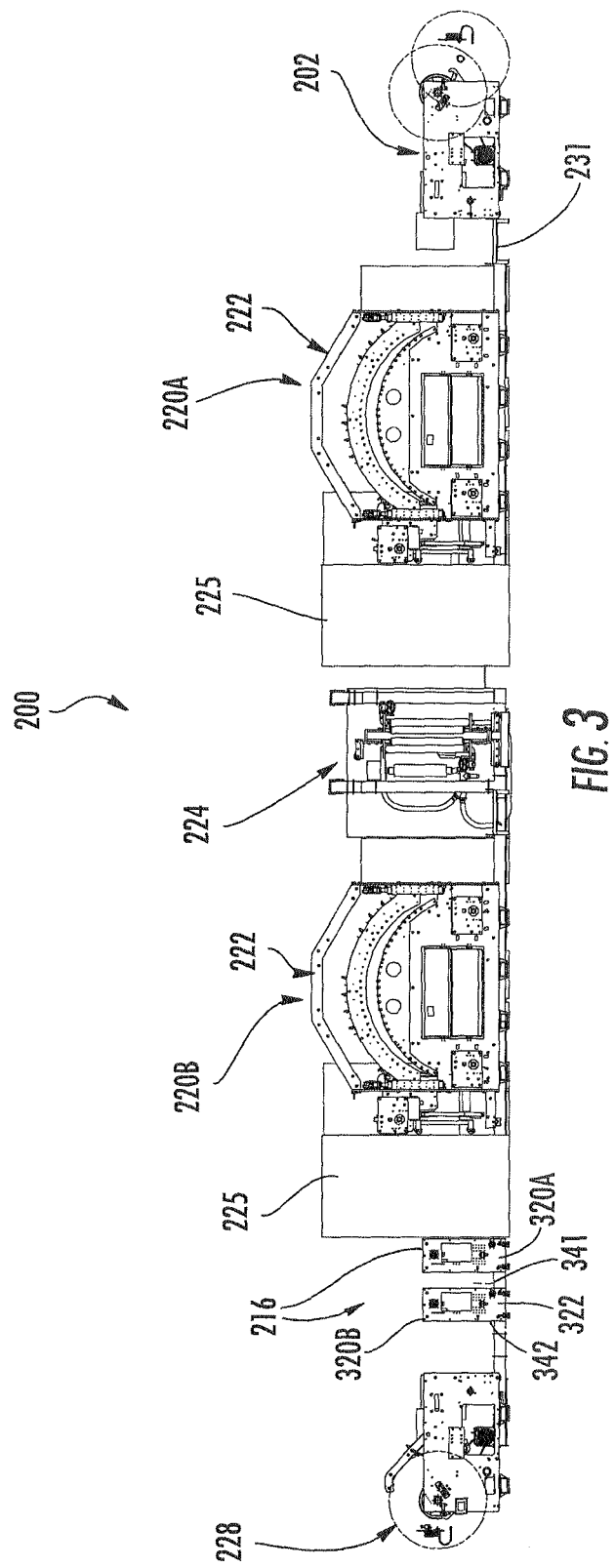
FIG. 3 is a side elevational view of another embodiment of the duplexing system of FIG. 2 according to an example embodiment.
Figure 4:
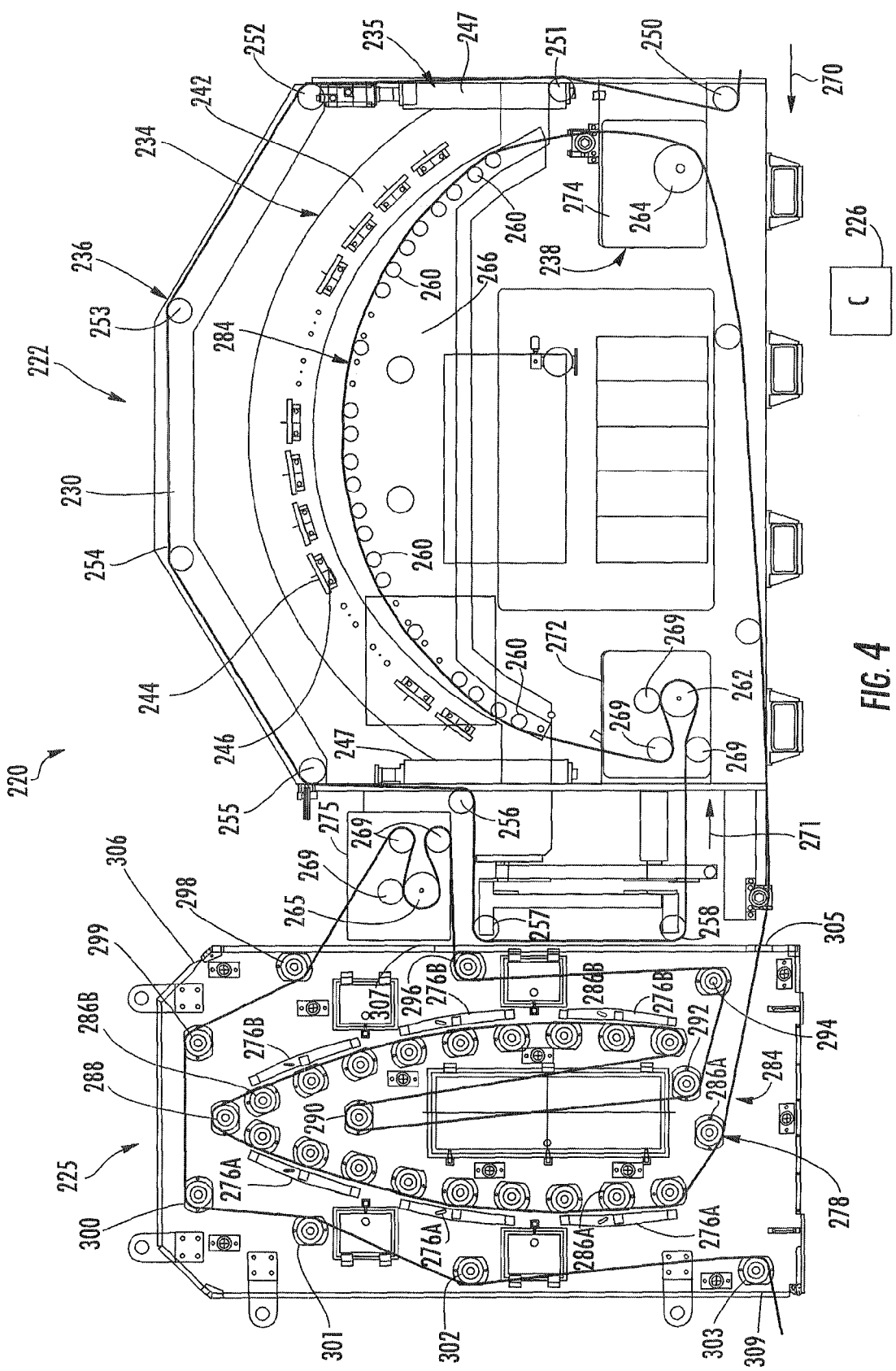
FIG. 4 is a side elevational view of a printing system of the duplexing system of FIG. 3 according to an example embodiment.
Figure 5:
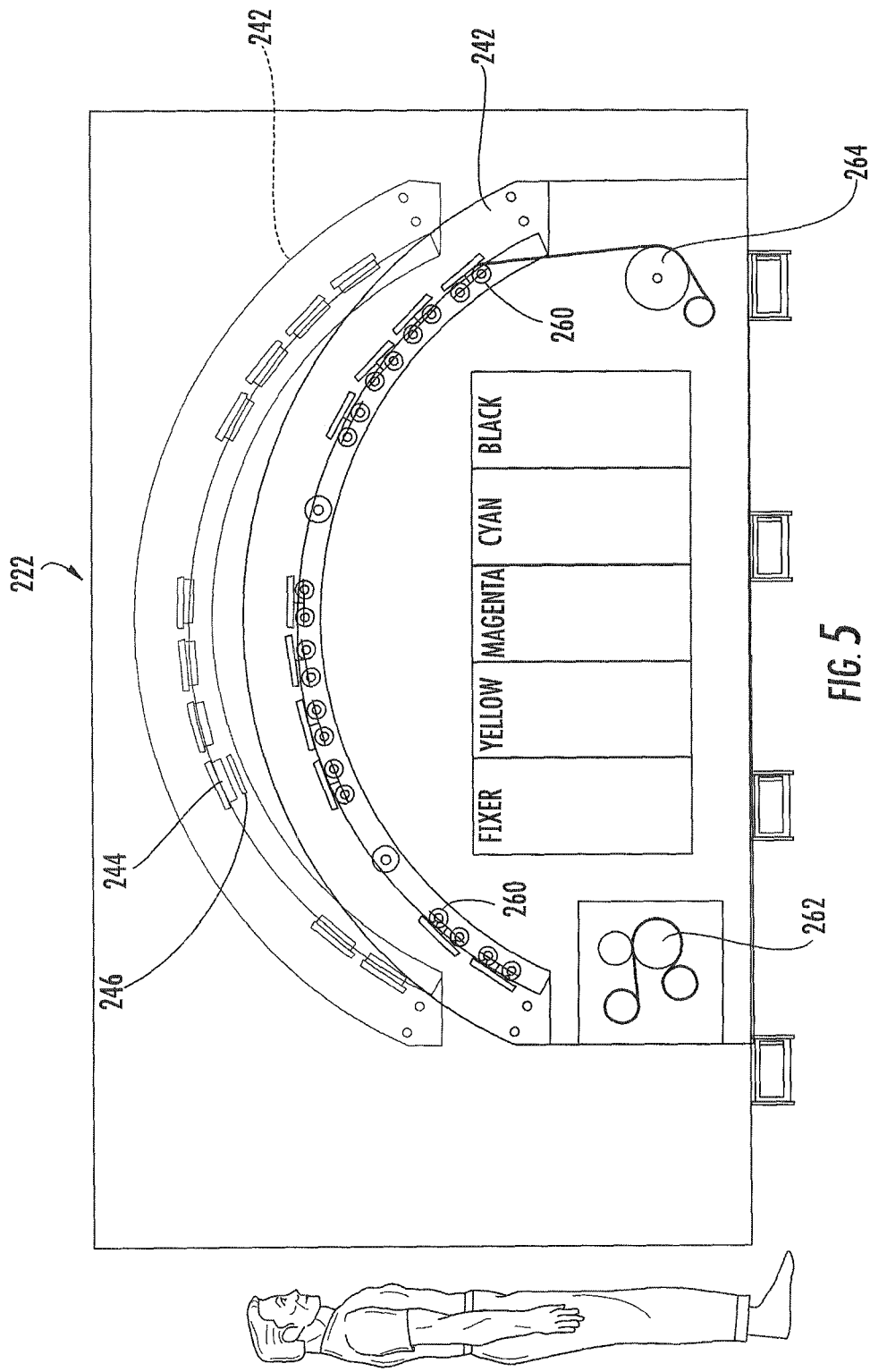
FIG. 5 is a side elevation of view of a print module of the printing system of FIG. 4 illustrating print heads in raised and lowered positions according to an example embodiment.

FIGS. 3-8 illustrate printing system 200, a particular embodiment of duplexing system 100. FIG. 5 schematically illustrates a print module 222 of the duplexing system 200. Duplexing system 200 is configured to print upon opposite sides of a web of media. Like duplexing system 100, duplexing system 200 includes a vision system 216 formed from two vision system modules 320, particular examples of vision system module 20. Using vision system 216, duplexing system 100 is further able to verify the print performance for print quality achieved on both faces of a web 130. As a result, enhanced quality control is achieved and adjustments may potentially be made to duplexing system 200 to enhance its printing performance.

In addition to vision system 216, duplexing system 200 includes web supply 202, printing systems 220A, 220B (collectively referred to as printing systems 220), web inverter 224, and web collector 228. Web supply 202 comprises a supply of web 230 which is unwound and delivered to printing system 220A across a walkway or intermediate platform 231.

Printing systems 220 are substantially identical to one another. Printing systems 220 are configured to print on opposite sides of web 230. In addition, printing systems 220 are configured to fix the printing material upon web 230. As shown by FIG. 3, each printing system 220A, 220B includes a print module 222 and a fixer module 225. Printing system 220A receives a web of media and prints upon a first face of the web in print module 222. The first face of the web is dried in fixer module 225 of system 220A.

Web inverter 224 comprise a mechanism configured to invert, flip or turn over the web of printing material such that system 220B prints upon a second opposite face of the same web. In the example embodiment illustrated, inverter 224 comprises any commercially available air driven turn bar or turn unit. In other embodiments, web inverter 224 may comprise other mechanisms or devices between systems 220A and 220B configured to flip or overturn a web of media.

Printing system 220B receives the overturned web and prints upon the second opposite side of the web using print module 222. Fixer module 224 dries the second opposite side of the pages that have been printed upon. Thereafter, the web, having been printed on both sides, is directed to vision system 216.

FIGS. 4 and 5 illustrate one of printing systems 220 in more detail. As shown by FIG. 4, system 220 includes print module 222, fixer module 225 and controller 226 (schematically shown). Print module 222 selectively deposits printing material upon web 230 to form an image, pattern, layout or arrangement of printing material upon web 230. In one embodiment, web 230 may comprise a web of printing material such as by cellulose-based media. In another embodiment, web 230 may comprise a web of polymeric material. In yet another embodiment, web 230 may comprise one or more other materials. In one embodiment, the printing material comprises a fluid such as one or more inks. In yet other embodiments, the printing material may comprise other types of fluid.

Print module 222 includes a printer 234, actuator 235, web flow path 236 and web drive 238. Printer 234 comprises a device or mechanism configured to selectively deposit printing material. Printer 234 includes support 242 and one or more pens or cartridges 244. Support 242 comprises a structure configured to support cartridges 244 opposite to web 230. In the particular example illustrated, support 242 is configured to support cartridges 244 along an arc opposite to web 230. In the embodiment illustrated, support 242 is movable towards and away from web 230. In yet another embodiment, support 242 is stationary opposite to web 30.

Cartridges 244 comprise mechanisms configured to eject fluid onto web 230. In the particular example illustrated, cartridges 244 each include one or more print heads 246 (schematically shown on one of cartridges 244). In one embodiment, print heads 246 each comprise thermal resistive drop-on-demand inkjet print heads. In yet other embodiments, print heads 246 may comprise piezo resistive inkjet print heads. In still other embodiments, print heads 246 may comprise other mechanisms configured to eject fluid in a controlled manner.

According to one embodiment, cartridges 244 each include a self-contained reservoir of fluid which is applied to the associated print heads 246. In yet another embodiment, cartridges 244 each include a reservoir which is further supplied with fluid or ink via an off-axis ink supply system using one or more pumps or other mechanisms to supply a fluid to each of cartridges 244. In one embodiment, cartridges 244 of printer 234 are configured to apply multiple colors of ink. In the embodiment illustrated, cartridges 244 are configured to deposit black (K), cyan (C), magenta (M) and yellow (Y) colored inks. In the example illustrated, printer 234 is additionally configured to apply a fixer (F) to web 230 prior to application of the colored inks. In other embodiments, printer 234 may include a fewer or greater number of such cartridges configured to apply a fewer or greater number of such different types of fluid.

Actuator 235 comprises a mechanism configured to selectively raise and lower support 242 to raise and lower cartridges 244 relative to web flow path 236 and web 230. As a result, support 242 may be moved to facilitate enhanced access to cartridges 244 for inspection, repair or replacement. In some embodiments, movement of support 242 and cartridges 244 may further facilitate servicing of print heads 246.

In the embodiment illustrated, actuator 235 comprises one or more hydraulic or pneumatic cylinder assemblies 247. In another embodiment, actuator 235 comprises one or more electric solenoids. In the yet another embodiment, actuator 235 may comprise one or more cams driven by one or more motors. In such an embodiment, support 242 may be supported by one or more support rods or other support structures. In still other embodiments, actuator 235 may be omitted.

Web flow path 236 comprises a path formed by one or more stationary or movable structures along which web 230 is supported and moved. In the particular example illustrated, web flow path 236 is formed by overhead rollers 250, 251, 252, 253, 254, 255, 256, 257 and 258, arcuately arranged rollers 260 and control rollers 262, 264, 266. Rollers 250-258 support and direct web 230 along path 236 over, around and about print support 242 and cartridges 244 generally to control roller 262. Although path 236 is illustrated as utilizing rollers 250-258 for directing web 230 over and around support 242, in other embodiments, path 236 may include a greater or fewer of such rollers for directing web 230 around support 242. In still other embodiments, other structures may be used to support web 230 over and around support 242. For example, stationary structures such as arcuate panels or plates may be used to support or direct web 230 around support 242.

Arcuately arranged rollers 260 comprise a series of rotationally supported cylinders or rollers supported in an arc by a support 266 opposite to support 242 and cartridges 244. In one embodiment, support 266 supports rollers 260 which rotate about their individual axes. Rollers 260 facilitate relatively smooth movement of web 230 with minimal friction upon web 230. In other embodiments, rollers 260 may include a greater or fewer number of such rollers or may include other structures configured to support web 230 in an arc opposite to support 242. For example, in another embodiment, rollers 260 may be replaced with one or more arcuate platens or plates.

Control rollers 262, 264 comprise independently rotationally driven rollers which define or form web flow path 236 and which move web 230 along web flow path 236. Roller 262 is located immediately upstream of cartridges 244 and their associated print heads 246. Roller 264 is located immediately downstream of cartridges 244 and their associated print heads 246 along web flow path 236. Rollers 262 and 264 form or define a printing zone across support 266 and rollers 260. Rollers 262 and 264 are configured to be driven at different speeds, facilitating adjustment of the tension of web 230 across and opposite to cartridges 244 during printing upon web 230. At the same time, rollers 262 and 264 may be driven at substantially the same speed, facilitating precise velocity control of web 230 across the printing zone formed by rollers 262, 264 and rollers 260.

Control roller 266 comprises an independently rotationally driven roller which further partially defines web flow path 236. Control roller 265 engages or contacts web 230 after web 230 has left printer module 222 and has passed through fixer module 225. In operation, control roller 265 pulls web 230 partially through fixer module 225 despite being physically associated with printer module 222. Because printer module 222 includes control roller 265, the cost and complexity of media treatment module 225 is reduced. Likewise, control of the velocity of control roller 265 may be more easily facilitated using controller 226 which is also physically associated with print module 222. In other embodiments, control roller 265 may alternatively be provided as part of fixer module 225.

As further shown by FIG. 4, each of control rollers 262 and 266 is preceded and succeeded by additional support rollers 269. Support rollers 269 facilitate wrap of web 230 about control rollers 262 and 265. In other embodiments, such additional support rollers 269 may be omitted.

As further shown by FIG. 4, web flow path 236 is inverted multiple times. In particular, when entering print module 222, web flow path 236 is flowing in a first direction as indicated by arrow 270. At roller 258, the direction in which web 230 is moving is inverted such that web 230 is redirected and moves in a second opposite direction as indicated by arrow 271. Web flow path 236 continues in an arc over rollers 260 opposite to cartridges 244 until it is once again inverted at roller 264 to once again flow in the direction indicated by arrow 270. Web flow path 236 continues to flow "downstream" in the direction indicated by arrow 270 until leaving print module 222 for a first time prior to reentering print module 222 at control roller 265.

Web drive 238 comprises one or more mechanisms configured to rotationally drive rollers 262, 264 and 265. In the example illustrated, web drive 238 comprises servo motors 272, 274 and 275 (with associated encoders). In other embodiments, web drive 238 may comprise other controllable sources of torque. In still other embodiments, web drive 238 may comprise a single motor configured to selectively supply distinct levels of torque or velocity to rollers 262, 264 and 265 using one or more transmissions and clutch mechanisms.

Fixer module 225 comprises an arrangement of components configured to treat printing material that is deposited upon web 230 by printer 234 of printer module 222 such that it attains a more permanent or steadfast characteristic or state, wherein the printing material is less susceptible to smearing, scratching, damage or alteration when being contacted or pressed upon. Fixer module 225 includes media treatment devices 276A, 276B (collectively referred to as media treatment devices 276) and web flow path 278. In the example illustrated, media treatment devices 276 comprise devices configured to dry printing material upon web 230. In one embodiment, media treatment devices 276 comprise devices configured to blow heated air onto one or more faces of web 230. In another embodiment, heaters 276 may additionally or alternatively apply infrared heat or other forms of the heat or energy, such as microwaves, to dry the printing material upon web 230.

In the particular example illustrated, media treatment devices 276 include one or more media treatment device 276 substantially facing in direction 270 and one or more media treatment device 276 substantially facing in direction 271, wherein web flow path 278 supports web 230 between such opposite media treatment devices 276 with the printed upon face of web 230 facing outwardly towards each of the opposed sets of one or more media treatment devices 276. In addition, as with media treatment device 276, media treatment devices 276 are substantially vertical. Thus, fixer module 225 and system 220 are more compact and occupy less floor space.

Web flow path 278 comprises an arrangement of one or more structures configured to support and direct movement of web 230 through fixer module 225 and relative to media treatment devices 276. Web flow path 278 includes support rollers 286A, 286B (collectively referred to as support rollers 286), inverter roller 288, return roller 290, exit rollers 292, 294 and 296, and reentry and discharge rollers 298, 299, 300, 301, 302 and 303. Support rollers 286A direct web 230 from fixer module input opening 305, in the outer enclosure or housing 306, across and opposite to media treatment devices 276A with the printed upon face 284 of web 230 facing media treatment devices 276A. Likewise, support rollers 276B support and direct movement of web 230 opposite to media treatment devices 276B with face 284 facing media treatment devices 276B. Inverter roller 288 is located between rollers 286A and 286B. Web 230 wraps approximately 280 degrees about roller 288 as it changes direction from an upward direction when moving across media treatment device 276A to a substantially downward direction when moving across media treatment device 276B. Because web 230 is directed in this up-and-down vertical path, fixer module 225 more effectively dries web 230 with fixer module 225 occupying less floor space. Because web flow path 278 supports movement of web 230 through at least three consecutive turns in a same direction immediately succeeding receipt of web 230 from print module 222, the printed upon face of web 230 is provided greater time for drying and for achieving a more permanent or robust state prior to being contacted.

Because web flow path 278 overlaps itself, the overall length of travel for the web is relatively large as compared to the floor space or volume occupied by fixer module 225, allowing more time for drying or other treatment of the web. At the same time, because web flow path 278 is bowed between such consecutive turns in the same direction, enhanced wrap of the web about and along the intermediate supports (such as the rollers shown) is enhanced, further enhancing transverse tracking of the web along such supports. Such transverse tracking is especially beneficial in fixer module 225 since the length of the path is elongated and undergoes multiple turns.

Return roller 290 comprises a rotationally supported roller between rollers 286A and 286B. As shown by FIG. 4, web 230 wraps about the last of rollers 286B and once again extends upwardly until wrapping about roller 290. After wrapping about roller 290, web 230 is directed vertically downward across roller 292, around roller 294 and outward after being supported by roller 296. Return roller 290 enables web 230 to once again pass between opposed heaters 276A and 276B for further heating and further drying. Thereafter, rollers 292-296 direct web 230 out discharge opening 307 formed in the outer enclosure or housing 306 of fixer module 225.

As shown by FIG. 4, web 230 is then directed from roller 296 about control roller 265 associated with printer module 222. After being driven by control roller 265, web 230 reenters web flow path 278 of fixer module 225. Rollers 298-303 support and direct web 230 over and around media treatment devices 276 down to a second discharge opening 309 in housing 306. Web 230 is discharged from fixer module 225 in substantially the same direction arrow 270 at which web 230 entered print module 222 of system 220. Consequently, web flow paths 236 and 278 enable system 220 to print and dry web 230 in an effective manner while occupying less floor space. Because web flow path 278 is a general teepee shape (a height at least greater to base and nominally two or more times greater than the base), the floor space occupied by fixer module 225 is even further reduced. In other embodiments, web flow path 278 may have other configurations.

Although fixer module 225 is illustrated as utilizing the illustrated serpentine web flow path 278 using the noted rollers, in another embodiment, fixer module 225 may utilize other serpentine web flow paths. In another embodiment, fixer module 225 may include other arrangements of rollers. In other embodiments, fixer module 225 may include other types of supports for guiding web 230 and directing movement of web 230 through fixer module 225. In some embodiments, fixer module 225 may include other types of media treatment devices or media treatment devices differently arranged within fixer module 225.

During printing by each printing system 220, controller 226 generates control signals directing motors 272, 274 and 275 to rotationally drive control rollers 262, 264 and 265, respectively, so as to control the tension and velocity of web 230. In particular, controller 226 generates control signals controlling the application of torque provided by rollers 262 and 264 to control the velocity and positioning of web 230 across rollers 260 opposite to print heads 246 of cartridges 244. At the same time, controller 226 generates control signals directing actuator 235 to position cartridges 244 into close proximity to face 284 of web 230. Controller 226 generates control signals directing fluid or printing material, such as ink, to be ejected onto face 284 by print heads 246.

Controller 226 also generates control signals controlling the amount of heat provided by media treatment devices 276. At the same time, controller 226 generates control signals directing motor 275 to rotationally drive control roller 265 to control the tension and velocity of web 230 through fixer module 225. In one embodiment, controller 226 may be configured to operate in different modes at different times based upon commands received via an input 226 or based upon instructions contained in an associated computer readable medium or memory. For example, in one embodiment, controller 226 may initially adjust the tensioning of web 230 by causing rollers 262 and 264 to be driven at different velocities. Once an appropriate tension has been set, controller 226 may generate control signals causing rollers 262, 264 to be driven at substantially the same velocity to control positioning of web 230 during printing. As web 230 is being moved through system 220, controller 226 may also generate control signals causing rollers 265 to be driven at a speed or velocity distinct from rollers 262 and 264. As a result, controller 226 may control the tension of the web 230 as it is being dried. This tension may be different from the tension of the web 230 across the print zone (across rollers 260 and opposite to cartridges 244).

At certain points in time, cartridges 244 or their print heads 246 may be repaired, replaced or serviced. At such times, controller 226 may generate control signals causing actuators 235 to raise or lift support 242 and cartridges 244 away from rollers 260 and that portion of web flow path 236 between rollers 260 and cartridges 244. FIG. 5 illustrates support 242 in a raised, servicing position as compared to the lowered, deployed and printing position. Consequently, system 220 enables access to print heads 246 from both above and below for replacement and servicing.

As shown in FIG. 4, printer module 222 and fixer module 225 comprise separate and distinct modules contained in separate and distinct enclosures or housings, wherein such modules are positioned in close proximity or adjacent to one another to facilitate transfer of web 230 therebetween. Because system 220 includes distinct modules 222, 224, printer module 222 may be used independently of fixer module 225 either by itself or with other fixer modules. Likewise, fixer module 225 may be used independently of printer module 222. In other embodiments, the components of print module 222 and fixer module 225 may alternatively be housed or contained within a single enclosure or housing.

Once both sides or faces of web 230 have been printed upon, web 230 is directed to vision system 216 (FIG. 3). Vision system 216 includes two substantially identical vision system modules 320A, 320B (collectively referred to as modules 320). FIGS. 6-8 illustrate modules 320 in more detail. FIG. 6 illustrates module 320B with its outer enclosure (shown in FIG. 3) substantially removed. FIG. 7 illustrates module 320B in more detail with web 230 being supported through module 320B. FIG. 8 illustrates module 320B positioned end to end with respect to a substantially identical vision system module 320A and further illustrates web 230 being directed through modules 320A and 320B.

As shown by FIGS. 6 and 7, vision system module 320 includes frame or enclosure 322 (shown in FIG. 3), track 324, cameras 326, and web supports 330, 332, 334, 336, 338 and 340. Enclosure 322 comprises one or more structures configured to support and at least partially enclose the remaining elements and components of vision system module 320B (or 320A). In the example illustrated, enclosure 322 substantially surrounds and completely encloses remaining components of vision system module 320. Enclosure 322 includes inlet 341 (FIG. 3) and outlet 342 (FIG. 3). Inlet 340 and outlet 342 comprise openings in walls of enclosure 322 through which a web enters and leaves enclosure 322 and vision module 320, respectively. Because enclosure 322 supports each of the remaining components and elements of vision system module 320, vision system module 320, when not receiving a web, may be transported, stored and repositioned as a self-contained unit independent of any other components or modules of a printing system. This modularity provides module 320 with enhanced versatility and increased flexibility with respect to a layout or arrangement of a printing system.

Track 324 (FIGS. 6-8) comprises one or more structures configured to movably support camera 326 with respect to a web passing through module 320. In one embodiment, track 324 is configured to movably support cameras 326 along an axis 343 across web 230, transverse to a direction in which web 230 is moving. In another embodiment, track 324 may be configured to movably support one or more cameras 326 along an axis substantially parallel to the direction in which the web 230 is moving. In one embodiment, track 324 comprises a bar having opposite grooves which slidably receive corresponding opposing projections or tongues extending from cameras 326. In another embodiment, the sliding movement of cameras 326 along track 324 may be facilitated by low friction surfaces or bearings. Because track 324 movably supports cameras 326 with respect to web 230 passing through module 320, cameras 326 may be repositioned with respect to the web to sense images or printing upon various portions of a face of a web or to accommodate different web widths. In yet another embodiment, track 324 may be omitted, wherein cameras 326 are stationarily supported by enclosure 322 or wherein cameras 326 rotate with respect to enclosure 322.

Cameras 326 comprise one or more image capture devices configured to sense or capture printing or other images upon a surface, such as a face of a web passing through module 320. Electrical signals representing a captured image are then transmitted from cameras 326 to controller 226 (shown in FIG. 4) or another processor, computer or other device for analysis and potentially used to improve print quality. In one embodiment, cameras 326 may comprise one or more video or still image charge coupled sensing devices. In other embodiments, other sensing cameras may be employed.

Web supports 330-340 comprise structures configured to support and direct a web through vision system module 320 and relative to cameras 326 while allowing a face of the web to be sensed by cameras 326. In the example illustrated, web supports 330-340 comprise freely rotating or idling rollers. Web support 332, sometimes referred to as an inspection cylinder, specifically comprises a roller platen against which web 230 bears against or is stretched during image capture by cameras 326. Web support 332 has a diameter to provide sufficient web rap to provide the web with a sufficiently flat surface or shape opposite to camera 326.

Web support 334, also known as an encoder roll, comprises a cylinder operably coupled to or including a sensor or encoder 343 which transmits electrical signals to controller 226 (shown in FIG. 4) regarding web position and speed. Web support 334 has a precise diameter to provide sufficient web wrap to provide accuracy with respect to web travel and encoder output. Web support 334 is positioned low enough to provide sufficient web wrap about web support 332 for camera focus, but high enough such that the web may be fed to support 332 without interference from support 334 and without additional supports to space the web from support 332. In other embodiments, web support 334 may be at other locations.

In other embodiments, web supports 330-340 may comprise platens, belts, stationary straight or curved web contacting panels, web contacting bearing surfaces or structures and the like. In particular embodiments, some of web supports 330-338 may be additionally configured to grip and drive a web along an associated web path. Web supports 330-340 form, define or provide a first web path 346 shown in FIG. 8 in which a web is presented opposite cameras 326 and a second alternative web path 348 (FIG. 7) in which the web is overturned prior to being presented opposite to one or both of cameras 326. Because web supports 330-340 provide two alternative web paths 346, 348, regardless of the orientation of the web as it enters module 320A or 320B, module 320A or 320B may be used to sense either face of a web depending upon which path the web takes through module 320. Consequently, module 320 is extremely versatile, allowing either face of a web to be sensed or allowing two substantially identical modules to be combined for sensing both faces of a web.

As shown by FIG. 8, web supports 334, 332 and 340 form web path 346. When directed through web path 346, the face 350 of web 230 that faces in an upward direction when entering module 320A (or module 320B) is the same face that is presented to cameras 326 for image capture. When web 230 exits the particular module 320, face 350 also faces in an upward direction. As shown by FIG. 8, web 230 initially wraps partially around web support 334. Web 230 then partially wraps around web support 332, comprising a roller platen, which is positioned opposite to cameras 326 and where the printed image or patterns upon face 350 are sensed or captured. After such capture, web 230 wraps at least partially about web support 340 before exiting the particular module 320.

As shown by both FIGS. 7 and 8, when directed through web path 348, the face 350 of web 230 that faces in an upward direction when entering module 320B (or module 320A) is overturned such that the opposite face 352 (the face of web 230 facing downward when entering a particular module 320) faces upward and is presented to cameras 326 for image capture. When web 230 exits the particular module 320, face 352 once again faces in a downward direction (as seen in FIGS. 7 and 8). As shown by FIG. 7, web 230 is initially supported by web support 330 below web support 334. Web 230 is substantially wrapped about web support 332 where it is overturned such that face 352 is presented to cameras 326. Thereafter, web 230 partially wraps about web support 334 where it is overturned once again and directed up to web supports 336 and 338. Web supports 336 and 338 direct web 230 over and across a back side of cameras 326. Thereafter, web 230 is directed to web support 340 which directs web 230 out of the particular module 320a, 320B.

As shown in FIG. 8, web paths 346 and 348 share several web supports. In particular, both web paths 346 and 348 utilize web supports 330, 332, 334 and 340. The web 230 wraps about web support 332 in opposite directions in paths 346 and 348. In particular, web 230 wraps about web support 332 and 346 in a counter-clockwise direction. In web path 348, web 230 wraps about web support 332 in a clockwise direction. Because modules 320 utilize the same web supports or share the same web supports in both web paths 346, 348, modules 320 are less complex, less expensive and more compact.

As web 230 is directed through a particular module 320 and is sensed by one or both of cameras 326, cameras 326 detect or verify the quality or accuracy of the printed image upon both sides of the web. Cameras 326 transmit or communicate signals representing the results to controller 226 (shown in FIG. 4) which adjusts operating parameters based upon the sense results. For example, in response to signals from one or both of cameras 326, controller 226 may adjust the velocity of the web 230, the tension of the web 230, the spacing or positioning of support 242 and cartridges 244 relative to the web or printing parameters of print heads 246, or the output of media treatment devices 276 of print system 220A.

Figure 9:
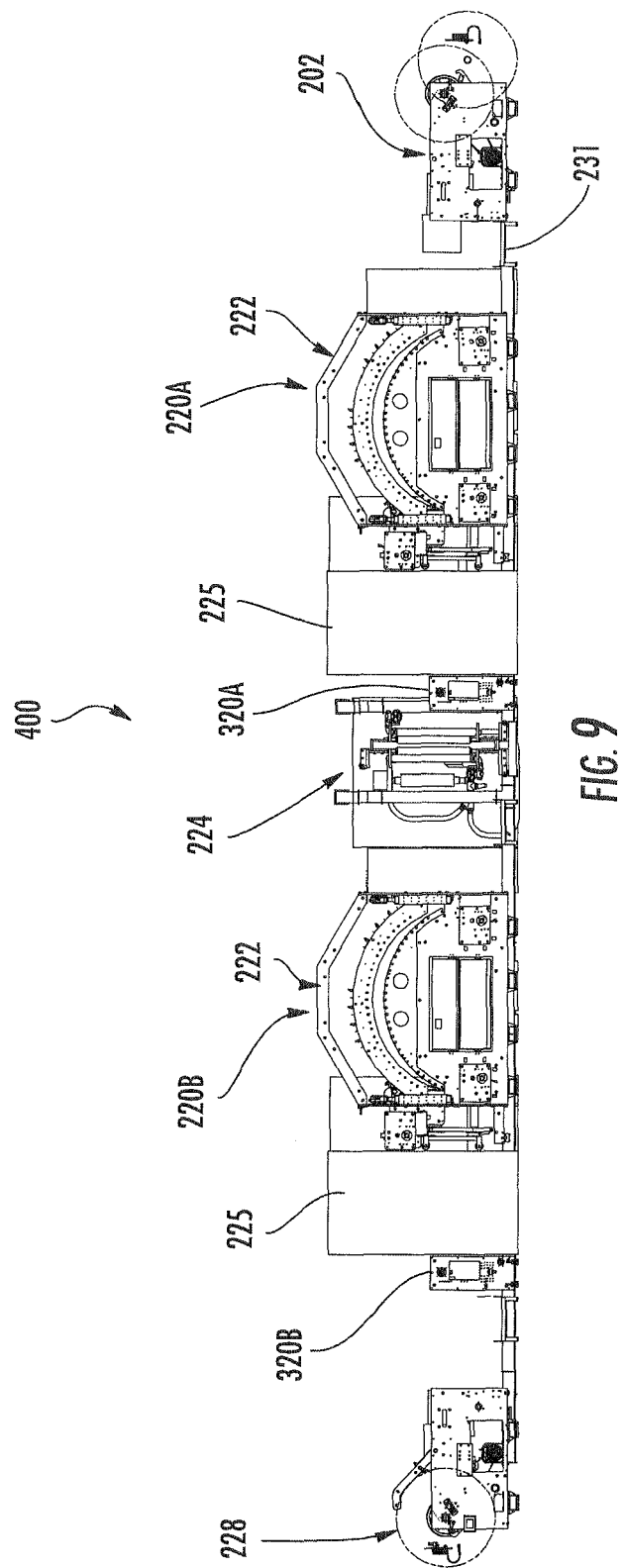
FIG. 9 is a side elevational view of another embodiment of the duplexing system of FIG. 2 according to an example embodiment.

FIG. 9 illustrates duplexing system 400, another embodiment of duplexing system 200. Duplexing system 400 is substantially identical to duplexing system 200 except that vision system modules 320A and 320B are provided at different locations. In particular, module 320A is positioned between printing systems 220A and 220B. Module 320B is positioned after printing system 220B. Those remaining components of duplexing system through 400 which correspond to elements of duplexing system 200 are numbered similarly. As shown by FIG. 9, because modules 320 are modular, are identical to one another and provide a straight and an overturning web path, each of modules 320 may be selectively interchanged at various locations along a duplexing system. In other embodiments, a single one of modules 320 may be employed where a single printing system 220 is used for printing on a single side of a web 230.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompasses a plurality of such particular elements.

What is claimed is:

1. An apparatus comprising:
   a first camera; and
   first web supports configured to form a first web path in which a web is presented opposite to the camera and an alternative second web path in which the web is overturned prior to being presented opposite of the first camera.

2. The apparatus of claim 1, wherein the first web path is contained on one side of the first camera and wherein the second web path also extends on an opposite side of the first camera.

3. The apparatus of claim 1 further comprising a first frame supporting the first camera and the first web supports.

4. The apparatus of claim 3, wherein the first frame, the first camera and the first web supports form a first module and wherein the apparatus further includes a second module identical to the first module and adjacent the first module.

5. The apparatus of claim 4 further comprising a web extending along the first web path in the first module and the second web path in the second module such that both faces of the web are captured by a camera.

6. The apparatus of claim 1 further comprising a track movably supporting the camera relative to the web path.

7. The apparatus of claim 1, wherein the first web path and the second web path each include a same roller platen opposite the camera.

8. The apparatus of claim 1, wherein the first web supports comprise:
   a first roller platen opposite to the camera;
   a first roller on a first side of the roller platen below the roller platen;
   a second roller on a second side of the first roller platen below the first roller platen;
   a third roller on the first side of the roller platen above the first roller platen and above the camera; and
   a fourth roller t e second side o first roller platen above the first roller platen and above the camera.

9. The apparatus of claim 8 further comprising a fifth roller on the first side of the roller platen below the roller platen.

10. The apparatus of claim 8, wherein the third roller and the fourth roller form the second web path and are omitted from the first web path.

11. The apparatus of claim 8, wherein the first web path directs the web in a first direction across the first roller platen and wherein the second web path directs the web in a second opposite direction across the first roller platen.

12. The apparatus of claim 8, wherein the first web path and the second web path are each configured such that the web is first engaged by the web supports on a first side of the roller platen and is lastly engaged b the web supports on a second opposite side of the roller platen.

13. The apparatus of claim 1 further comprising one or more print devices configured to print a first side of the web.

14. A method comprising:
   providing first and second modules each having two alternative web paths for passing a web through that module, said alternative web paths comprising substantially identical first web paths, one in each module, and substantially identical second web paths, one in each module;
   moving a web along the first web path of the first module, sensing a first face of the web while the web moves along the first web path of the first module;
   moving the web along the second web path of the second module; and
   sensing a. second face of the web while the web moves along the second web path of the second module.

15. The method of claim 14 further comprising:
   contacting the second face of the web with a first roller platen of the first module opposite a first camera of the first module; and
   contacting the first face of the web with a second roller platen of the second module opposite a second camera of the second module.

16. An apparatus comprising:
   at least one web inspection module comprising:
      a camera; and
      two alternative web paths through said module such that a first of said alternative web paths presents a first side of a web to said camera for inspection and a second of said alternative web paths presents a second side of said web to said camera for inspection.

17. The apparatus of claim 16, wherein said first web path passes along only one side of said camera and said second web path extends around said camera.

18. The apparatus of claim 16, further comprising:
   a printer module;
   a fixer module;
   a control roller disposed on said printer module; and
   a web path that extends from said printer module, into said fixer module and to said control roller, such that said control roller on said printer module pulls a web in said web path through a portion of said fixer module.

19. The apparatus of claim 18, wherein said web path, after leaving said control roller, reenters said fixer module and then exits said fixer module to said web inspection module.

20. The apparatus of claim 16, further comprising a fixer module, wherein a web path in said fixer module overlaps itself to allow more time for fixing printing on a web.

* * * * *

UNITED STATES PATENT AND TRADEMARK OFFICE
CERTIFICATE OF CORRECTION

PATENT NO. : 8,593,635 B2  
APPLICATION NO. : 13/119705  
DATED : November 26, 2013  
INVENTOR(S) : Paul C. Ray et al.

Page 1 of 1

It is certified that error appears in the above-identified patent and that said Letters Patent is hereby corrected as shown below:

In the Claims

In column 14, line 1, in Claim 8, delete "t e" and insert -- on the --, therefor.

In column 14, line 1, in Claim 8, delete "o" and insert -- of the --, therefor.

In column 14, line 15, in Claim 12, delete "b" and insert -- by --, therefor.

In column 14, line 18, in Claim 13, delete "print" and insert -- print on --, therefor. (2nd occurrence)

In column 14, line 60, in Claim 19, delete "reenters" and insert -- re-enters --, therefor.

Signed and Sealed this  
Fifteenth Day of April, 2014

Michelle K. Lee  
*Deputy Director of the United States Patent and Trademark Office*